(12) United States Patent
Ito

(10) Patent No.: US 9,194,865 B2
(45) Date of Patent: Nov. 24, 2015

(54) OBJECT SELECTING DEVICE AND OBJECT SELECTING METHOD

(75) Inventor: Saburo Ito, Shizuoka-ken (JP)

(73) Assignee: YAMAHA HATSUDOKI KABUSHIKI KAISHA, Shizuoka-ken (JP)

( * ) Notice: Subject to any disclaimer, the term of this patent is extended or adjusted under 35 U.S.C. 154(b) by 0 days.

(21) Appl. No.: 14/361,999

(22) PCT Filed: Dec. 19, 2011

(86) PCT No.: PCT/JP2011/007072
§ 371 (c)(1),
(2), (4) Date: May 30, 2014

(87) PCT Pub. No.: WO2013/093954
PCT Pub. Date: Jun. 27, 2013

(65) Prior Publication Data
US 2014/0322747 A1    Oct. 30, 2014

(51) Int. Cl.
*G01N 1/00* (2006.01)
*G01N 33/50* (2006.01)
(Continued)

(52) U.S. Cl.
CPC ........ *G01N 33/5091* (2013.01); *B01D 21/2483* (2013.01); *B01L 3/502761* (2013.01); *C12M 47/04* (2013.01); *G01N 15/0272* (2013.01); *G01N 33/48728* (2013.01);
(Continued)

(58) Field of Classification Search
CPC .......... B07B 1/00; B07B 1/04; B07B 1/4609; B07B 1/469; B07B 2230/01; B01L 3/50255; B01L 3/502753; B01L 3/502761; G01N 1/4088; G01N 15/0272; B01D 21/0012; B01D 21/0039

USPC ................................................... 506/7, 8, 39
See application file for complete search history.

(56) References Cited

U.S. PATENT DOCUMENTS 5,262,128 A    11/1993 Leighton et al.
6,338,802 B1 *  1/2002 Bodner et al. ............... 210/650
(Continued)

FOREIGN PATENT DOCUMENTS

CN    1307001 C    3/2007
DE    19850233 A1    5/2000
(Continued)

OTHER PUBLICATIONS

International Search Report; PCT/JP2011/007072; Mar. 6, 2012.
(Continued)

*Primary Examiner* — Joseph C Rodriguez
(74) *Attorney, Agent, or Firm* — Studebaker & Brackett PC

(57) ABSTRACT

An object selecting device includes a container configured to store liquid, a plate configured to support a selection object by being immersed into the liquid stored in the container, and a holder configured to hold the plate in a state where a bottom surface of the plate and an inner bottom part of the container are separated. The plate includes a through hole at a support position. The through hole includes a tapered portion configured to allow the selection object to precipitate along a direction of gravity and support the selection object in contact with the inner wall surface of the through hole. An opening area at the upper end of the tapered portion is larger than that at the lower end of the tapered portion. Only the selection object can be supported out of the collection of objects having different shapes.

17 Claims, 14 Drawing Sheets

(51) Int. Cl.
  *C12M 1/00* (2006.01)
  *G01N 33/487* (2006.01)
  *B01L 3/00* (2006.01)
  *G01N 15/02* (2006.01)
  *B01D 21/24* (2006.01)

(52) U.S. Cl.
  CPC . *B01L 2300/0681* (2013.01); *B01L 2300/0829* (2013.01); *B01L 2400/0439* (2013.01)

(56) References Cited

U.S. PATENT DOCUMENTS

| | | | |
|---|---|---|---|
| 6,485,690 B1* | 11/2002 | Pfost et al. | 422/552 |
| 6,589,779 B1 | 7/2003 | McDevitt et al. | |
| 6,602,702 B1 | 8/2003 | McDevitt et al. | |
| 7,666,360 B2* | 2/2010 | Schellenberger et al. | 422/552 |
| 8,105,554 B2* | 1/2012 | Kanigan et al. | 422/504 |
| 8,911,687 B2* | 12/2014 | Huang et al. | 422/534 |
| 8,968,682 B2* | 3/2015 | Hale | 422/534 |
| 9,052,298 B2* | 6/2015 | Reed et al. | 1/1 |
| 2002/0094533 A1 | 7/2002 | Hess et al. | |
| 2002/0121529 A1 | 9/2002 | Hoummady | |
| 2003/0003036 A1* | 1/2003 | Rouleau et al. | 422/245.1 |
| 2003/0219716 A1* | 11/2003 | Avdeef et al. | 435/4 |
| 2004/0121432 A1 | 6/2004 | Klein et al. | |
| 2006/0252047 A1* | 11/2006 | Ekstrom et al. | 435/6 |
| 2006/0257994 A1 | 11/2006 | Noda et al. | |
| 2009/0071834 A1* | 3/2009 | Hafeman et al. | 204/641 |
| 2010/0248981 A1* | 9/2010 | Shirazi | 506/9 |
| 2011/0065590 A1* | 3/2011 | Hunter | 506/7 |
| 2011/0201530 A1* | 8/2011 | Oldham et al. | 506/39 |
| 2014/0341680 A1* | 11/2014 | Ito | 414/222.01 |
| 2014/0370589 A1* | 12/2014 | Ito | 435/309.1 |

FOREIGN PATENT DOCUMENTS

| | | |
|---|---|---|
| EP | 1722235 A1 | 11/2006 |
| JP | 05-103658 A | 4/1993 |
| JP | 06-328002 A | 11/1994 |
| JP | 2006-317345 A | 11/2006 |
| JP | 2009-504161 A | 2/2009 |
| JP | 2010-233456 A | 10/2010 |
| WO | 91/05519 A1 | 5/1991 |
| WO | 01/06239 A2 | 1/2001 |
| WO | 2002/030561 A2 | 4/2002 |
| WO | 02/081075 A1 | 10/2002 |
| WO | 2007/022026 A2 | 2/2007 |
| WO | 2011/129348 A1 | 10/2011 |
| WO | 2011/149013 A1 | 12/2011 |

OTHER PUBLICATIONS

The extended European search report issued by the European Patent Office on Jun. 9, 2015, which corresponds to European Patent Application No. 11877936.2-1553.

* cited by examiner

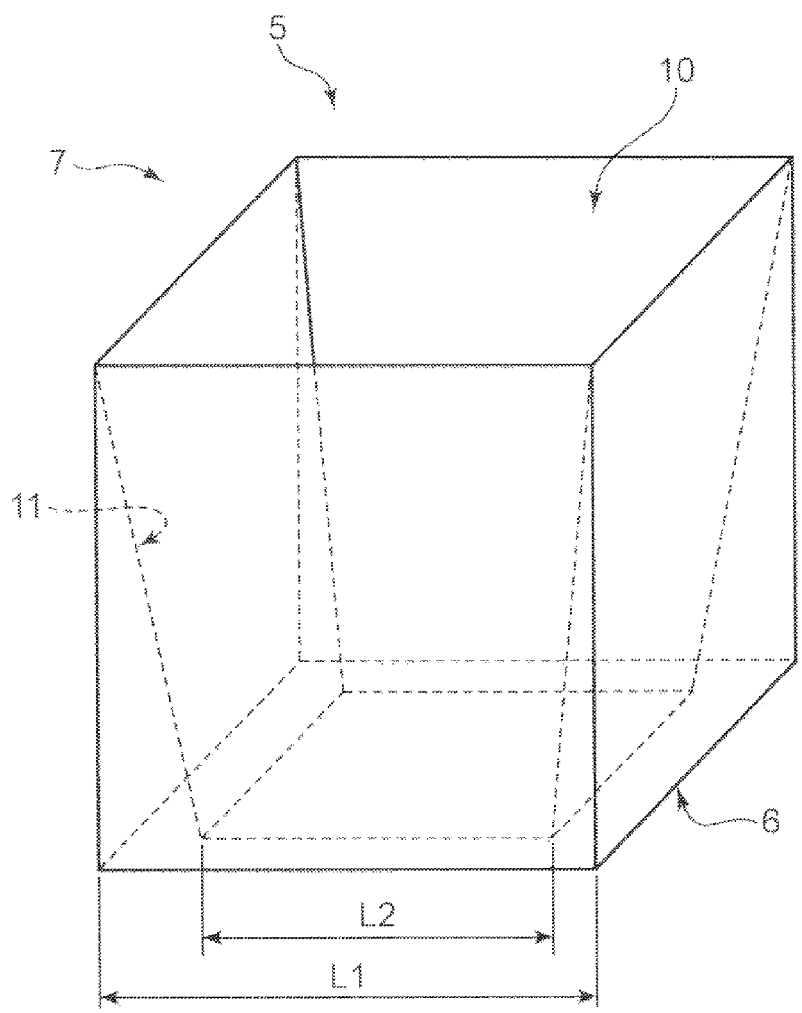

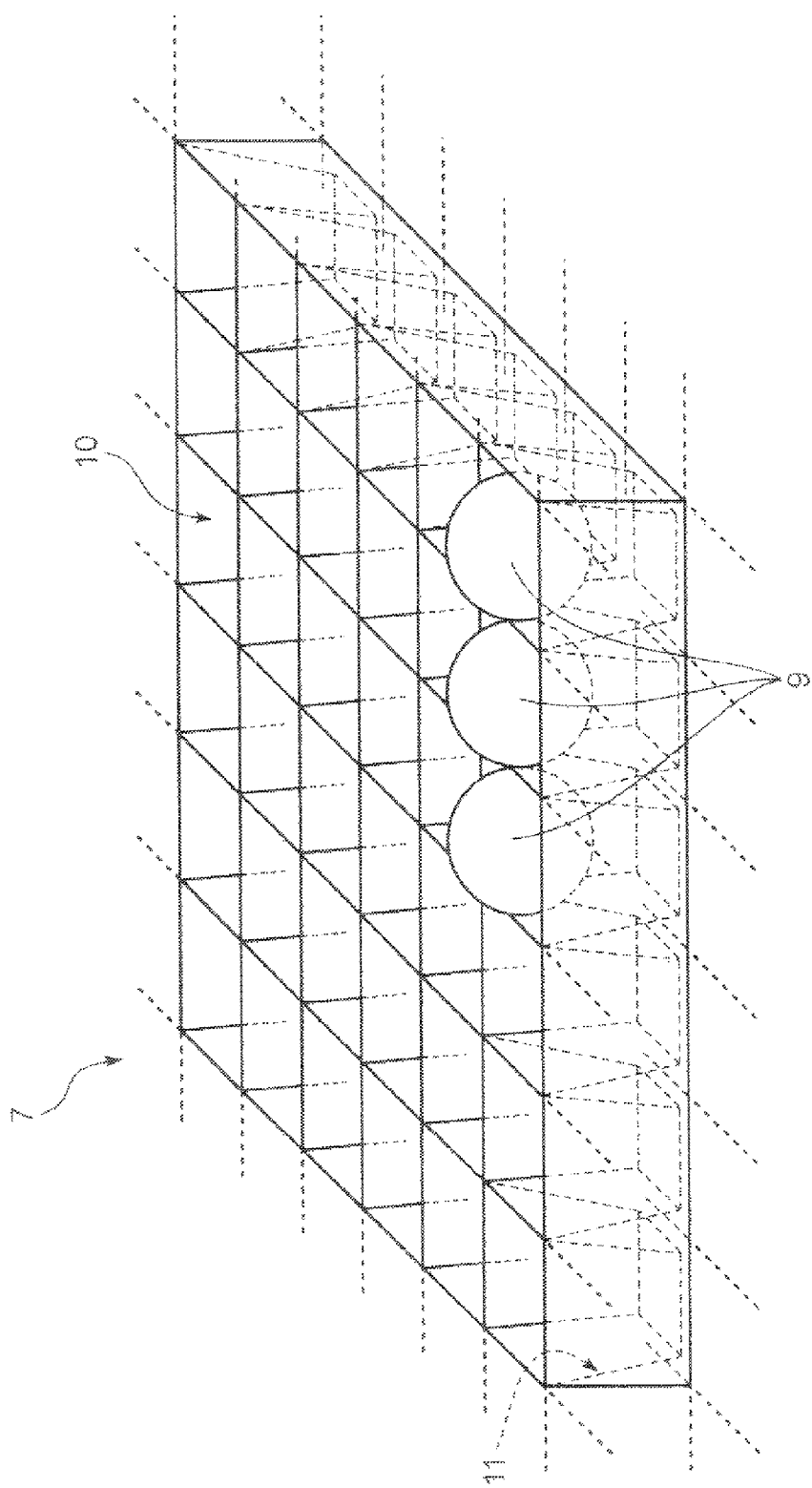

FIG. 9A
FIG. 9B
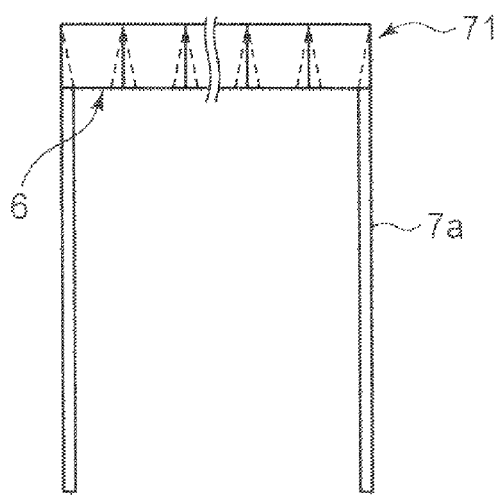
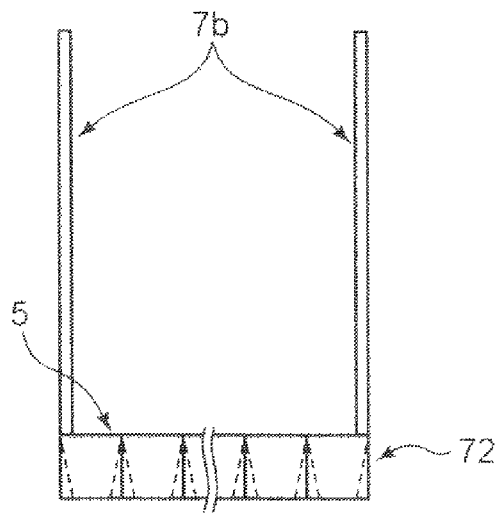

OBJECT SELECTING DEVICE AND OBJECT SELECTING METHOD

CROSS REFERENCE TO RELATED APPLICATION

This application claims benefit of priority to International Patent Application No. PCT/JP2011/007072 filed on Dec. 19, 2011, the entire content of which is incorporated herein by reference.

TECHNICAL FIELD

The present disclosure relates to an object selecting device and an object selecting method. More specifically, the present disclosure relates to an object selecting device and an object selecting method for selecting only a selection object of a predetermined shape from a collection of objects having different shapes.

BACKGROUND

Conventionally, in various fields, sieving devices have been used to select particles according to size or outer shape (hereinafter, these are referred to merely as shape). Larger particles to be selected include tablets, capsules and granulated granules and smaller ones including bio-based cells used in the fields of bio-related technology and medicine.

If, for example, cells are selected to make the shape uniform in this way, deviations of test conditions can be made smaller in various tests using such cells. The selected cells can be subjected to high-throughput screening (HTS) and the like.

However, an operation of selecting only objects shaped to be suitable for a test not only from tablets and capsules, but also from a plurality of cells having various shapes is very difficult.

In view of such a problem, Japanese Unexamined Patent Publication (Japanese translation of PCT application) No. 2009-504161 discloses a method for manufacturing a platen having a desired thickness and formed with a plurality of through holes. The platen of Japanese Unexamined Patent Publication (Japanese translation of PCT application) No. 2009-504161 includes the plurality of through holes and selects cells by supporting cells and the like in the through holes. Further, Japanese Unexamined Patent Publication No. H05-103658 discloses a selecting device for selecting capsules dyed with a dye. The selecting device of Japanese Unexamined Patent Publication No. H05-103658 includes a holding container having a mesh in which the capsules are to be arranged and a pipette for causing only the capsules satisfying conditions to pass through mesh openings by giving a water flow and selecting only such capsules by suction. Further, Japanese Unexamined Patent Publication No. 2006-317345 discloses a particle capture device provided with a nozzle capable of reliably sucking one particle from a plurality of particles having different outer diameters without depending on outer diameters. The particle capture device of Japanese Unexamined Patent Publication No. 2006-317345 includes a vibration generator for lifting a plurality of precipitated particles by applying vibration, and the particles lifted by vibration are sucked by the nozzle for selection.

SUMMARY

However, in the case of sucking cells supported by the platen formed with the through holes disclosed in Japanese Unexamined Patent Publication (Japanese translation of PCT application) No. 2009-504161 or capsules supported on the mesh disclosed in Japanese Unexamined Patent Publication No. H05-103658 by a selection nozzle, there is a problem that this nozzle not only sucks the cells or capsules to be selected, but also simultaneously sucks smaller cells and particles having passed through the through holes and the mesh openings. Further, in the case of generating vibration by the vibration generator disclosed in Japanese Unexamined Patent Publication No. 2006-317345, there is a problem that small cells and particles precipitated on an inner bottom part of a container are blown up and sucked by the selection nozzle without being distinguished from the selection objects since the vibration generator is provided at a position to vibrate the container.

Accordingly, the technique disclosed in any of these publications is not a technique for selecting selection objects suitable for test conditions based on the shape, and there is a problem of being unable to select only a selection object (particularly bio-based cell aggregate) having a predetermined shape from a collection of objects having different shapes.

The present disclosure was developed in view of such conventional problems and aims to provide an object selecting device and an object selecting method capable of selecting only a selection object having a predetermined shape from a collection of objects having different shapes.

An object selecting device according to one aspect of the present disclosure includes a container including an inner bottom part and configured to store liquid, a plate having a top surface and a bottom surface and configured to support a selection object by being immersed into the liquid stored in the container, and a holder configured to hold the plate in a state where the bottom surface of the plate and the inner bottom part of the container are separated, wherein the plate includes a through hole at a support position for the selection object, and the through hole includes a tapered portion configured to allow the selection object to precipitate along a direction of gravity and support the selection object in contact with the inner wall surface of the through hole in a state where the plate is immersed in the liquid in the container, an opening area at the upper end of the tapered portion being larger than an opening area at the lower end of the tapered portion.

An object selecting method according to another aspect of the present disclosure is a method for selecting a selection object from a collection of objects including the selection object, and includes an immersion step of immersing a plate having a top surface and a bottom surface and configured to support a selection object and a holder configured to hold the plate with the bottom surface of the plate and an inner bottom part of a container separated in the container including the inner bottom part and storing liquid, a precipitation step of adding a collection of objects including the selection object to the liquid from a side of the top surface of the plate and causing the collection of objects to precipitate along a direction of gravity into a through hole formed in the plate, arranged at a support position where the selection object is supported and including a tapered portion on the inner wall surface thereof, an opening area at the upper end of the tapered portion being larger than an opening area at the lower end of the tapered portion, and an arrangement step of bringing the selection object out of the collection of objects precipitating in the through hole into contact with the tapered portion and supporting the selection object at the support position.

An object, features and advantages of the present disclosure will become more apparent upon reading the following detailed description along with the accompanying drawings.

BRIEF DESCRIPTION OF THE DRAWINGS

FIG. 2 is a perspective view showing a through hole of the first embodiment of the present disclosure.

FIG. 4 is a perspective view showing another example of a plate of the first embodiment of the present disclosure.

FIGS. 9A and 9B are diagrams showing holder of a second embodiment of the present disclosure.

DETAILED DESCRIPTION

Object Selecting Device

First Embodiment

Figure 1:
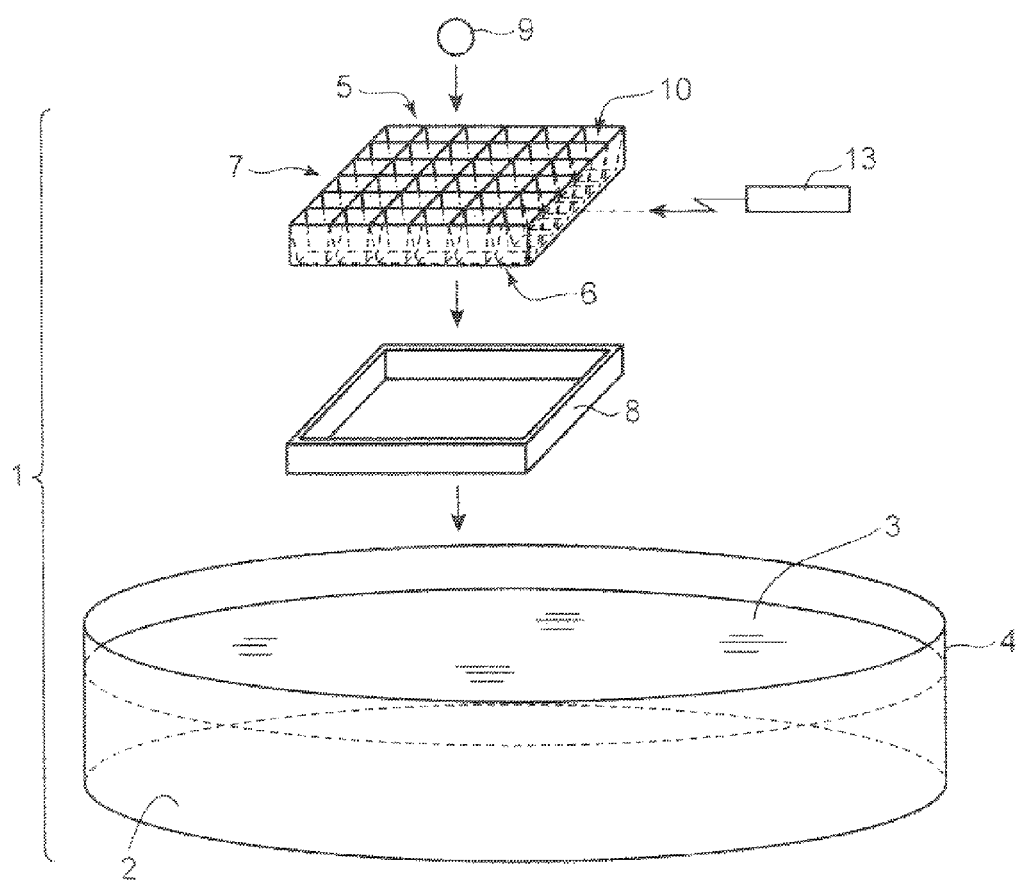
FIG. 1 is a diagram showing the configuration of an object selecting device of a first embodiment of the present disclosure.

Hereinafter, an object selecting device 1 of a first embodiment of the present disclosure is described in detail with reference to the drawings. FIG. 1 is a diagram showing the configuration of the object selecting device 1 of the first embodiment of the present disclosure.

The object selecting device 1 of this embodiment includes a container 4 including an inner bottom part 2 and configured to store liquid 3, a plate 7 having a top surface 5 and a bottom surface 6 and to be immersed in the liquid 3 stored in the container 4, and a spacer 8 (holder) for holding the plate 7 in a state where the bottom surface 6 of the plate 7 and the inner bottom part 2 of the container 4 are separated. The plate 7 includes through holes 10 at support positions for selection objects 9. A vibration generation mechanism 13 (vibration generator) is connected to the plate 7. Each component is described below.

Selection Object 9

The selection objects 9 are objects to be selected from a collection of objects M (see FIG. 3B) using the object selecting device 1 of this embodiment.

The type of the collection of objects M is not particularly limited, but examples thereof include mixtures of particles having various shapes and particle diameters, cell culture solutions and cell treatment solutions containing cells and impurities having various sizes. For example, if the collection of objects M is mixed slurry of particles having various shapes and particles having a predetermined shape are selected using the object selecting device 1, the selected particles having the predetermined shape fall under the selection objects 9. Similarly, if the collection of objects M is a cell culture solution or a cell treatment solution including cells and impurities having various sizes and only cells having a predetermined shape are selected using the object selecting device 1, the selected sells having the predetermined shape fall under the selection objects 9.

Bio-based cells are objects having relatively large shape deviations. Thus, if the selection objects 9 are bio-based cells, cells having a uniform shape can be selected by using the object selecting device 1 of this embodiment. This can largely contribute to improved operation efficiency in the fields of bio-related technology and medicine. Particularly, if the selection objects 9 are bio-based cell aggregates (spheroids), a result considering functions of individual cells can be obtained as compared with a test result obtained using one cell since a biosimilar environment considering interactions among cells is reconfigured in the cell aggregate, and experiment conditions can be made uniform in accordance with an environment in a biological body. Thus, by using the object selecting device 1 of this embodiment, a highly reliable result can be obtained in the fields of bio-related technology and medicine.

Figure 13:
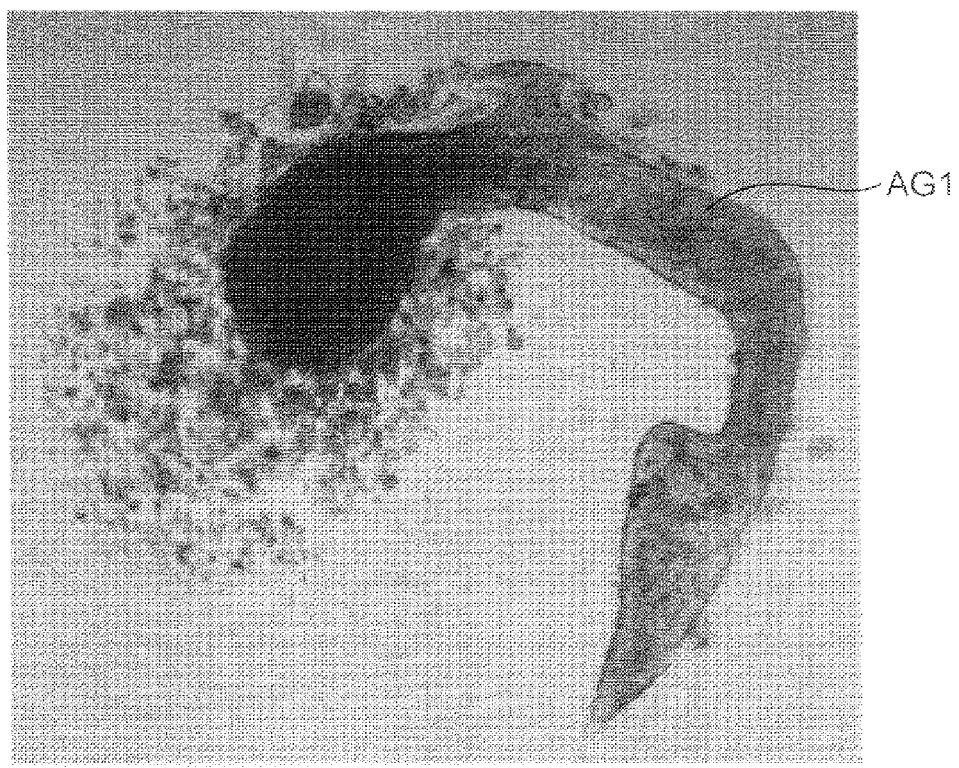
FIG. 13 is a micrograph of a cell aggregate having a distorted shape.
Figure 14:
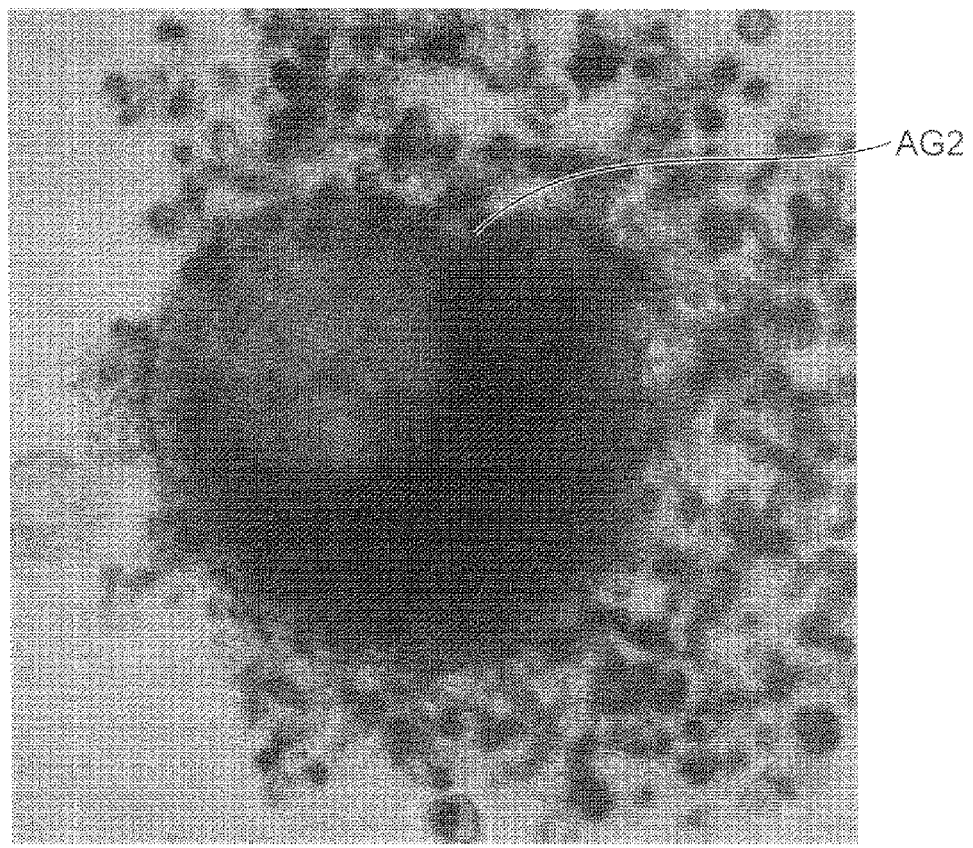
FIG. 14 is a micrograph of a cell aggregate with an uneven density.

Here, such a cell aggregate is generally formed by aggregating several to several hundred thousands of individual cells. Thus, cell aggregates vary in size. A cell aggregate formed by living cells has a substantially spherical shape. However, if some of the cells constituting a cell aggregate are altered or dead cells, the cell aggregate may become a cell aggregate AG1 having a distorted shape as shown in FIG. 13 or a cell aggregate AG2 with an uneven density as shown in FIG. 14. By using the object selecting device 1 of this embodiment, only cell aggregates having a shape suitable for a test can be selected from a plurality of cell aggregates having these various shapes.

Container 4

The container 4 stores the liquid 3. In FIG. 1, the container 4 is illustrated to be formed of a bottomed cylindrical body including the inner bottom part 2 and having an open upper end.

The shape of the container 4 is not particularly limited, but the inner bottom part 2 is preferably flat and having a relatively wide flat shape whose height is relatively smaller than a width is preferably adopted in terms of operability, stability and the like.

The container 4 has only to have such a size sufficient to store the liquid 3 to such an extent that the plate 7 to be described later can be completely immersed.

The material of the container 4 is not particularly limited, but it is preferable to use a translucent material in terms of possibility to easily confirm a state of a content stored in the container 4. Further, if both the container 4 and the plate 7 are made of a translucent material as described later, operation efficiency can be improved since the selection objects 9 can be continuously observed, for example, by a phase-contrast microscope from above or below the container 4.

The translucent material is not particularly limited, but it is preferable to use, for example, thermoplastic resins, thermosetting resins and photocurable resins. More specifically, the examples of the translucent material include polyethylene resins; polyethylene naphthalate resins; polypropylene resins; polyimide resins; polyvinyl chloride resins; cycloolefin copolymers; norbornene-containing resins; polyether sulfone resins; polyethylene naphthalate resins; cellophanes; aromatic polyamide resins; (meth)acrylic resins such as polymethyl (meth)acrylates; styrene resins such as polystyrenes and styrene-acrylonitrile copolymers; polycarbonate resins; polyester resins; phenoxy resins; butyral resins; polyvinyl alcohols; cellulose-based resins such as ethyl cellulose, cellulose acetate and cellulose acetate butyrate; epoxy resins; phenol resins; silicone resins; and polylactic acids.

It is also preferable to use inorganic materials such as metal alkoxides, ceramic precursor polymers, solutions obtained through hydrolysis polymerization of solutions containing metal alkoxides by a sol-gel method, or inorganic materials obtained by solidifying combinations of these such as inorganic materials having a siloxane bond (polydimethylsiloxane, etc.) and glass.

Soda glass, quartz, borosilicate glass, Pyrex (R) glass, low melting point glass, photosensitive glass and other optical glasses having various refractive indices and Abbe numbers can be widely used as the glass.

A circular glass dish having a height of several mm to several cm and a diameter of about 10 cm can be used as the container 4 satisfying these conditions.

The liquid 3 stored in the container 4 is not particularly limited if it does not degrade properties of the selection objects 9, and can be appropriately selected according to the type of the selection objects 9. Typical examples of the liquid 3 may include, for example, cell freezing solutions such as glycerol to be added before refrigeration storage and Cell Bankers (produced by Juji Field Inc.), formalin, reagents for fluorescent staining, antibodies, purified water and physiological saline solution in addition to media such as basic media, synthetic media, Eagle's media, RPMI media, Fischer's media, Ham's media, MCDB media and serums. If the selection objects 9 are cells, a culture preservation solution suited to the cells can be used. For example, in the case of using BxPC-3 (human pancreatic tumor cells), which are bio-based cells, as the selection objects 9, a mixture of a RPMI-1640 medium with 10% of FBS (Fetal Bovine Serum), to which a supplement such as antibiotic or sodium pyruvate is added if necessary, can be used as the liquid 3.

The amount of the liquid 3 stored in the plate 7 is not particularly limited and is preferably sufficient to completely immerse the plate 7 to be described later.

Plate 7

The plate 7 is used by being immersed in the liquid 3 stored in the container 4 together with the spacer 8 (holder) to be described later. The plate 7 includes through holes 10 at support positions where the selection objects 9 are supported. The plate 7 illustrated in FIG. 1 has a flat rectangular parallelepipedic shape having the top surface 5 and the bottom surface 6, and a plurality of through holes 10 penetrating from the top surface 5 to the bottom surface 6 are arranged in a 6×6 matrix.

The shape of the plate 7 is not particularly limited, but is preferably a flat shape because the plate 7 is easily immersed in the container 4 and the selection objects 9 are easily selected from the collection of objects M precipitated right below with gravity when the container 4 has a flat shape and because a microscope is easily focused in observing the objects supported at the support positions of the plate 7.

The plate 7 has only to have such a size with a width smaller than an opening width of the container 4 and a height smaller than a storage depth of the container 4 since the plate 7 needs to be immersed in the liquid 3 stored in the container 4.

The material of the plate 7 is not particularly limited, but a translucent material is preferably used because a state of a content can be easily confirmed. Further, as described later, if both the container 4 and the plate 7 are made of a translucent material, the selection objects 9 can be continuously observed, for example, by a phase-contrast microscope from above or below the container 4.

The translucent material is not particularly limited, but the materials described in the description of the container 4 can be used.

The plate 7 of this embodiment includes the through holes 10 vertically penetrating through the top surface 5 and the bottom surface 6 of the plate 7 at the support positions for the selection objects 9 as shown in FIGS. 1 and 2. FIG. 2 is a perspective view showing the through hole 10 of the first embodiment of the present disclosure.

The through hole 10 has a tapered portion 11. The tapered portion 11 is provided to allow the selection object 9 to precipitate along a direction of gravity and support the selection object 9 in contact with the inner wall surface of the through hole 10 in a state where the plate 7 is immersed in the liquid 3 in the container 4. An opening area at an upper end side of the tapered portion 11 is larger than that at a lower end side of the tapered portion 11. Specifically, the tapered portion 11 is a tapered portion whose opening area is gradually narrowed from the top surface 5 toward the bottom surface 6.

A procedure of selecting the selection objects 9 is described in detail later. The through holes 10 of the plate 7 capture only the selection objects 9 by the tapered portions 11 and allow non-objects 12 to pass as shown in FIGS. 3C and 3D.

Figure 3A:
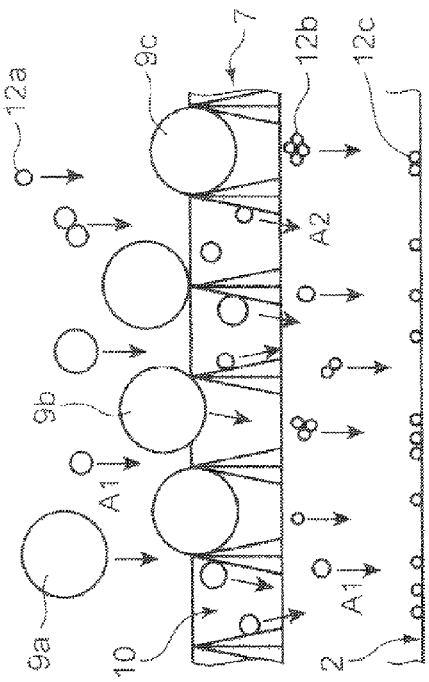
FIGS. 3A through 3D are diagrams showing a state of selecting selection objects in the object selecting device of the first embodiment of the present disclosure.
Figure 3B:
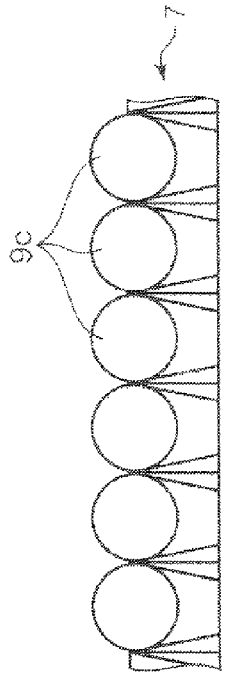
Figure 3C:
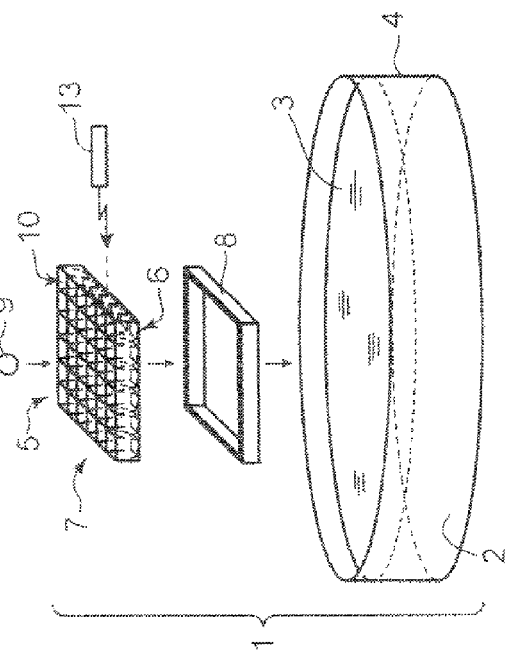

In FIG. 3C, reference sign 9a denotes a selection object precipitating in a direction of gravity A1 and reference sign 12a denotes a non-object precipitating in the direction of gravity A1. Reference sign 9b denotes a selection object precipitating in the through hole 10 and reference sign A2 denotes a direction of precipitation of the selection object 9b along the tapered portion 11. Since diameters of the non-objects 12a are smaller than the opening area at the lower ends of the tapered portions 11, the non-objects 12a pass through the through holes 10. Reference sign 12b denotes a non-object precipitating in the direction of gravity after passing through the through hole. The non-objects 12b having passed through the through holes 10 precipitate to the inner bottom part 2 of the container. Reference sign 12c denotes a non-object precipitated on the inner bottom part 2 of the container 4. In this way, the non-objects 12 having a diameter smaller than the opening area of the lower ends of the tapered portions 11 precipitate to the inner bottom part 2 of the container 4 without being supported by the tapered portions 11 of the through holes 10. Further, since the upper end edges of the tapered portions are pointed as shown in FIG. 3C, the selection objects 9a and the non-objects 12a are unlikely to be caught and easily introduced into the through holes 10.

Figure 3D:
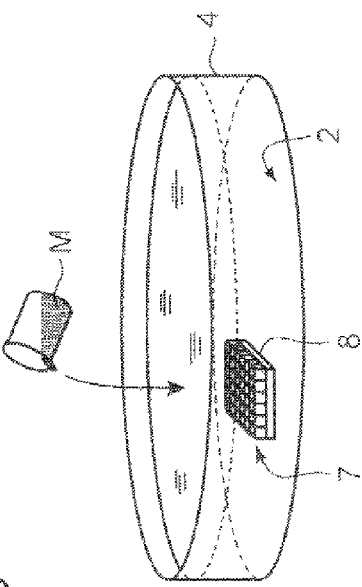

On the other hand, as shown in FIG. 3D, the objects having a diameter larger than the opening area of the lower ends of the tapered portions 11 out of the collection of objects M precipitated into the through holes 10 are held in contact with the inner wall surfaces of the tapered portions 11 and the through holes 10 and supported as the selection objects 9 (selection objects 9c). FIG. 3D is a diagram of the selection objects 9 supported in contact with the tapered portions 11. Reference number 9c denotes the supported selection object. Through the above process, the collection of objects M is selected into the selection objects 9 and the non-objects 12.

The number of the through holes 10 is not particularly limited. For example, the plate 7 may include only one through hole 10 as shown in FIG. 2. In this case, FIG. 2 is also a perspective view showing a modification of the plate 7 of the first embodiment of the present disclosure. A plurality of through holes 10 are preferable because a plurality of selection objects 9 can be simultaneously selected. Further, in the case of providing the plate 7 with a plurality of through holes 10, the through holes 10 are preferably arranged in a matrix as shown in FIG. 4. FIG. 4 is a perspective view showing the plate 7 in which the plurality of through holes are arranged in a matrix. The number of the arranged through holes is not particularly limited. In FIG. 4, the plate 7 is illustrated in which a total of thirty six through holes 10 are arranged in a 6×6 matrix. By forming many through holes 10 in one plate 7 in this way, the selection objects 9 having a predetermined shape can be simultaneously arranged and selected. As a result, operation efficiency can be drastically increased as compared with the case where the selection objects 9 are individually selected. Further, if a plurality of selection nozzles 14 corresponding to the arrangement of the through holes 10 are used in the case of extracting the selection objects 9 by the selection nozzles (extractor) (see FIG. 8) as described later, it can contribute to the automation of the device. As a result, the device can be used for high-throughput screening and the like and a work amount can be drastically reduced.

The shape of the through hole 10 is not particularly limited if the tapered portion 11 is formed as described above and the opening area at the upper end side is larger than that at the lower end side. The through hole 10 preferably has a frustum shape because the selection object 9 is easily inserted into the through hole 10 along the tapered portion 11 and because the substantially spherical selection object 9 is easily selected as compared with the case where the tapered portion 11 is provided only on a part of the inner wall surface of the through hole 10.

Types of the frustum shape may include truncated cone shapes, truncated pyramid shapes and the like. If the through hole 10 has a truncated pyramid shape, clearances are formed at the corners of the truncated pyramid in a state where the selection object 9 having a substantially spherical shape is supported by the tapered portion 11. As a result, the selection object 9 is not fitted into the through hole 10 and can be easily extracted. Above all, a truncated square pyramid shape and a truncated hexagonal pyramid shape are preferable because of easy processing and easiness to densely form many through holes 10 per unit area of the plate 7. Note that angles of inclination of the tapered portion 11 formed in the through hole 10 need not be equal. Further, a cross-sectional shape of the frustum shape (shape of the through hole when the plate 7 is observed from above) is not particularly limited and may have a cross-sectional shape other than a regular polygonal shape.

In FIG. 2, reference sign L1 denotes the length of one side of the opening at the top surface side of the through hole 10 when the through hole 10 is formed into a truncated square pyramid shape, and reference sign L2 denotes the length of one side of the opening at the bottom surface side of the through hole 10 when the through hole 10 is formed into a truncated square pyramid shape. A ratio ($L2^2/L1^2$) of the opening area at the bottom surface side ($L2^2$) to the opening area at the top surface side ($L1^2$) is preferably 0.11 to 0.94, more preferably 0.17 to 0.44 and even more preferably 0.18 to 0.31. If $L2^2/L1^2$ is within the above range, the plate 7, the selection objects 9 and the selection nozzle 14 (see FIG. 8) to be described later can be captured within a depth of field of a lens provided in a phase-contrast microscope while reducing the influence of the shadow of the plate 7 on observation when the supported selection objects 9 are observed from above or below the container 4, for example, by the phase-contrast microscope. Thus, a user can easily confirm whether or not the selection objects 9 are supported by the plate 7, and the shapes of the supported selection objects 9. Further, the user can confirm the positions of the selection objects 9 and the position of the selection nozzle 14. Furthermore, even if there is a slight flow of the liquid 3 in the container 4 such as when the collection of objects M is added to the liquid 4, the selection objects 9 supported by the plate 7 are more reliably supported by the plate 7 without flowing out of the through holes 10 by the flow.

Figure 5A:
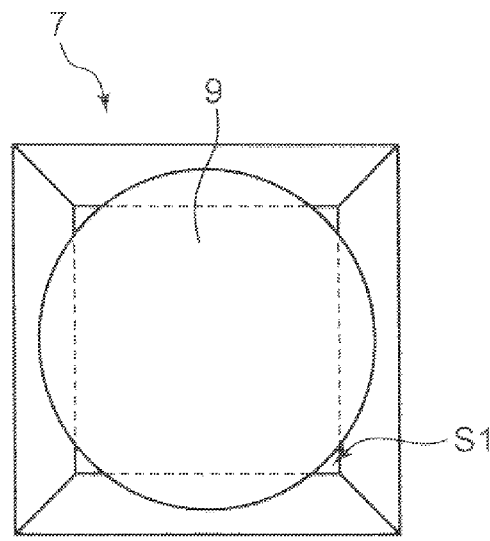
FIGS. 5A through 5C are plan views showing a state where a selection object is supported by the plate of the first embodiment of the present disclosure.
Figure 5B:
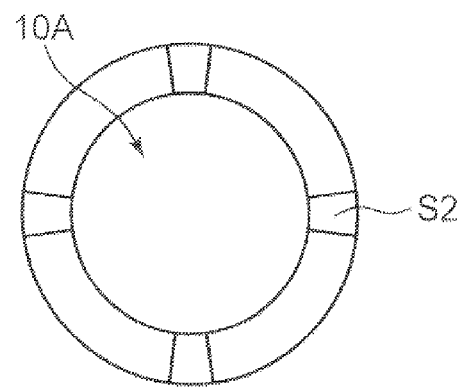
Figure 5C:
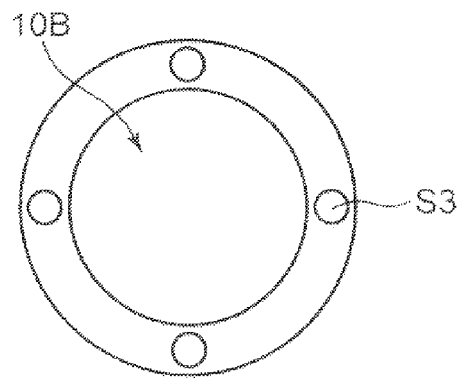
Figure 6:
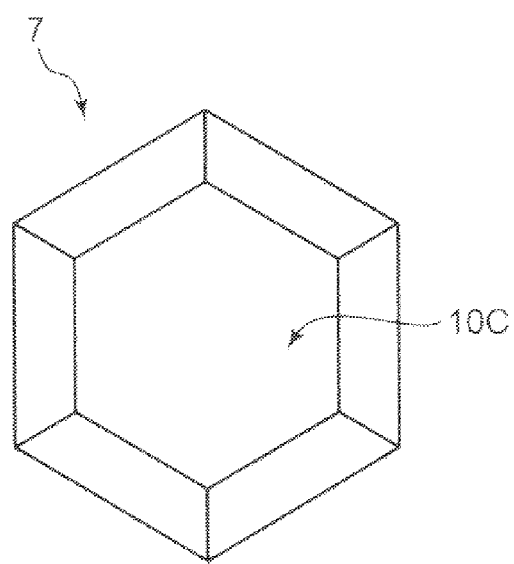
FIG. 6 is a top view showing another example of the plate of the first embodiment of the present disclosure.

Examples of the shape of the through hole 10 preferable from other perspectives are listed. FIG. 5A is a plan view showing a state where the selection object 9 is supported in the through hole 10 having a truncated square pyramid shape shown in FIGS. 2 and 4. FIG. 5B is a top view of a through hole 10A having a truncated cone shape. FIG. 5C is a top view of a through hole 10B having a truncated cone shape. FIG. 6 is a top view of a through hole 10 having a truncated hexagonal pyramid shape.

As shown in FIG. 5A, the through hole 10 is preferably shaped to form clearances S1 capable of allowing the flow of the liquid 3 from the bottom surface side to the top surface side of the through hole 10 with the selection object 9 supported by the plate 7. In FIG. 5, the truncated square pyramid shape is illustrated as the shape of the through hole. As described above, if the selection object 9 has a substantially spherical shape, the selection object 9 may be possibly fitted into the through hole 10 without forming any clearance depending on the shape of the through hole 10. In this case, there is a possibility of requiring an excessive force in extracting the selection object 9 by the selection nozzle 14 (see FIG. 8) to be described later. As a result, the selection object 9 may be possibly deformed if it is soft. Further, if the selection object 9 is a bio-based cell, there is a possibility that the cell will be destroyed and properties thereof are altered by the application of an excessive force.

However, if the clearances S are formed as described above, the selection object 9 is not fitted into the through hole 10 and liquid flow produced when the liquid 3 passes through the clearances S1 act on the selection object 9 as buoyancy. Thus, an excessive force is not required at the time of extraction by the selection nozzle 14. As a result, the selection object 9 can be easily extracted without being deformed or destroyed.

The through hole 10A shown in FIG. 5B is provided with grooves (clearance forming members S2) in parts of the tapered portion. If the selection object 9 enters the through hole 10A and is supported at a support position, the grooves serve as clearances formed between the selection object 9 and the through hole 10A. The through hole 10B shown in FIG. 5C is provided with projections (clearance forming members S3) on parts of the tapered portion. If the selection object 9 enters the through hole 10B and is supported at a support position, the projections come into contact with the selection object 9, wherefore clearances are formed between the selection object 9 and the tapered portion.

Spacer 8

As shown in FIG. 1, the spacer 8 (holder) is placed on the inner bottom part 2 of container 4 and the plate 7 is placed on the spacer 8. A hollow and flat square spacer is illustrated as the spacer 8. The spacer 8 is provided to hold the bottom surface 6 of the plate 7 and the inner bottom part 2 of the container 4 in a separated state. This is for allowing the non-objects 12 to pass through the through holes 10 and precipitate toward the inner bottom part 2 of the container 4 and separating the non-objects 12 from the selection objects 9 by holding the bottom surface 6 at a position higher than the inner bottom part 2. Thus, if the spacer 8 is not provided and the bottom surface 6 of the plate 7 and the inner bottom part 2 of the container 4 are proximate, distances between the selection objects 9 (see selection objects 9c of FIG. 3C)

selected and supported by the plate 7 and the non-objects 12 (see non-objects 12c of FIG. 3C) precipitated on the inner bottom part 2 of the container 4 become shorter. As a result, the non-objects 12 may also be erroneously extracted in extracting the selection objects 9 by the selection nozzle 14 (see FIG. 8). In this embodiment, by providing the spacer 8, the non-objects 12 precipitated on the inner bottom part 2 of the container 4 and the selection objects 9 selected and supported by the plate 7 are separated. As a result, the non-objects 12 precipitated on the inner bottom part 2 of the container 4 are not erroneously extracted in extracting the selection objects 9 from the plate 7.

Figure 7:
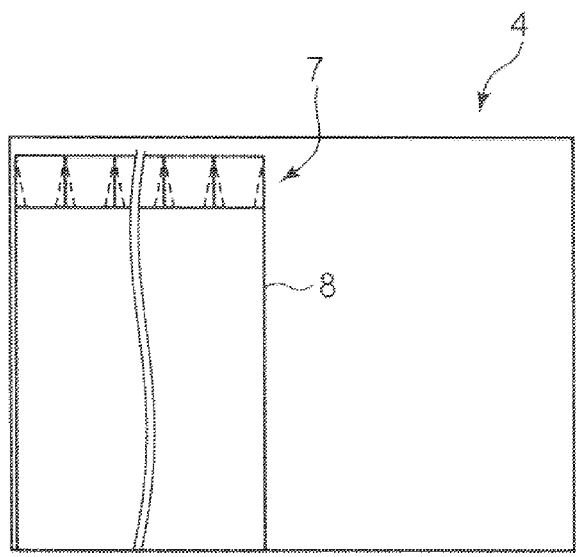
FIG. 7 is a side view showing a holder of the first embodiment of the present disclosure.

A method for separating the bottom surface 6 of the plate 7 and the inner bottom part 2 of the container 4 is not particularly limited. It is possible to adopt a method for inserting a member like the above spacer 8 between the bottom surface 6 of the plate 7 and the inner bottom part 2 of the container 4, a method for separating the bottom surface 6 of the plate 7 and the inner bottom part 2 of the container 4 by providing a leg unit on the bottom surface 6 of the plate 7 or another method. In this embodiment, the method for inserting the spacer 8 is adopted as shown in FIGS. 1 and 7. FIG. 7 is a side view showing the spacer 8 of this embodiment.

The size (length, height) of the spacer 8 has only to be set to have a height sufficient to immerse the plate 7 in the liquid 3 with the plate 7 placed on the spacer 8 since the plate 7 needs to be immersed in the liquid 3 stored in the container 4. Further, the spacer 8 preferably has a height capable of sufficiently separating the bottom surface 6 of the plate 7 and the inner bottom part 2 of the container 4. Furthermore, the height of the spacer 8 is preferably within a depth of field of an optical system of a microscope when the selection objects 9 supported by the plate 7 are observed from above or below the container 4 by the microscope. Although it depends on a method for extracting the selection objects 9, the weights and sizes of the non-objects 12, the height (depth) of the liquid 3 stored in the container 4 and the like, the non-objects 12 are not erroneously extracted if a spacing is about 100 to 5000 μm. In this embodiment, the spacer 8 having a height of 3000 μm is used.

The material of the spacer 8 is not particularly limited, but a translucent material is preferably used because it is easy to confirm a state of the selection objects 9 supported by the plate 7. The translucent material is not particularly limited, but the materials described in the description of the container 4 can be, for example, used.

The spacer 8 may be integrally fixed to the inner bottom part 2 of the container 4 or may be provided separately. In the case of separately providing the spacer 8, it is preferable to use a material having such a weight that the spacer 8 does not move in the liquid 3.

Vibration Generation Mechanism 13

As described above, since the collection of objects M precipitated toward the top surface 5 of the plate 7 precipitates with gravity, some of them may precipitate to be held on the top surface 5 of the plate 7 without being introduced into the through holes 10 and the non-objects 12 may deposit on the selection objects 9 already supported at the support positions besides precipitating into the through holes 10 provided at the support positions. Accordingly, the vibration generation mechanism 13 (vibration generator) (see FIG. 1) vibrates the plate 7 to apply vibration to the selection objects 9 held at positions of the plate 7 other than the support positions and prompt them to move to the support positions. If elliptical non-objects 12 (see FIG. 11) not having a substantially spherical shape and the like are caught in the through holes 10, this vibration generation mechanism 13 can also prompt them to pass through the through holes 10 and precipitate to the inner bottom part 2 of the container 4 by applying vibration. A vibrator connected to an external power source (not shown) and configured to apply vibration to the plate 7 can be, for example, illustrated as the vibration generation mechanism 13.

A method for vibrating the selection objects 9 by applying electromagnetic waves within such a range as not to affect the properties of the selection objects 9, a method for vibrating the selection objects 9 by applying ultrasonic waves and the like can be adopted as a vibration generation method by a vibration generator in addition to a method for generating physical vibration by the vibrator as the vibration generation mechanism 13.

Note that a procedure of applying vibration is not particularly limited. Vibration may be applied before the collection of objects M is added to the liquid 3 and continued until the selection of the selection objects 9 is finished or vibration may be applied after the elapse of a time after the collection of objects M is added to the liquid 3.

As just described, the vibration generation mechanism 13 of this embodiment is not provided for the container 4, but for the plate 7 and applies vibration to the plate 7. Thus, vibration is not propagated to the non-objects 12 precipitated on the inner bottom part 2 of the container 4 and the non-objects 12 are not blown up by vibration. As a result, the non-objects 12 remain precipitated on the inner bottom part 2 of the container 4 and the selection objects 9 and the non-objects 12 are physically separated, wherefore the non-objects 12 are not extracted in extracting the selection objects 9 by the selection nozzle 14 to be described later.

Selection Nozzle 14

The selection nozzle 14 (extractor) is provided to extract the selection objects 9 supported by the plate 7 from the plate 7.

Figure 8:
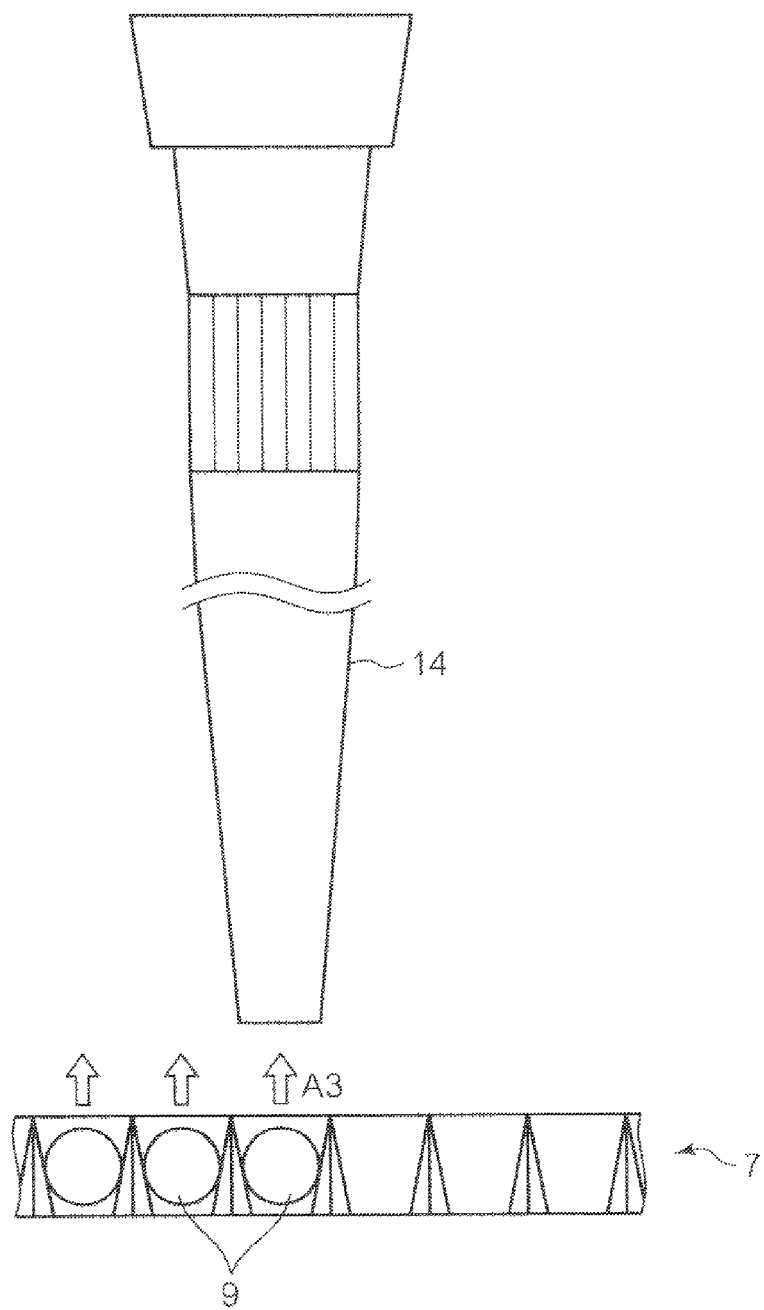
FIG. 8 is a diagram showing an extractor of the first embodiment of the present disclosure.

The extractor is not limited to the selection nozzle 14 and has only to adopt a method capable of extracting the selection objects 9 supported by the plate 7 without significantly deforming or destroying the selection objects 9. As shown in FIG. 8, an extraction method by suction using the selection nozzle 14 whose tip has a nozzle shape is illustrated in this embodiment. FIG. 8 is a diagram showing the extractor 14 of this embodiment. In FIG. 8, reference sign A3 denotes an extracting direction.

As just described, since the selection objects 9 can be extracted from the plate 7 and moved to a subsequent process by the selection nozzle 14 in this embodiment, the remaining plate 7 can be reused. Particularly, operation efficiency can be improved by automating the extraction by the selection nozzle 14. Note that the reuse of the plate 7 is not essential and the plate 7 can also be disposable.

As described above, according to the object selecting device 1 of this embodiment, it is possible to support only the selection objects 9 having the predetermined shape out of the collection of objects M having different shapes by the tapered portions 11 and allow the non-objects 12 other than the selection objects 9 to precipitate to the inner bottom part 2 of the container 4. Further, in the case of extracting the selection objects 9 supported by the tapered portions 11 such as by suction, the non-objects 12 precipitated on the inner bottom part 2 of the container 4 are not erroneously extracted since the plate 7 is held separated from the inner bottom part 2 of the container 4 by the spacer 8.

Note that a process performed by the user in this embodiment can be automatically performed using a robot by controlling the robot by software programming the content of the process in advance.

Further, although the selection objects 9 are cell aggregates and can be gently extracted such as by vertically inverting the plate 7 immediately after being supported by the plate 7 in this embodiment, the selection objects 9 may be kept for a predetermined time at the support positions of the plate 7 if necessary. For example, if the selection objects 9 are not sufficiently grown cell aggregates, but single cells or undergrown cell aggregates, the user can continue to cultivate these selection objects 9 kept supported at the support positions of the plate 7 and extract these selection objects 9 after the selection objects 9 have sufficiently grown. The extracted cell aggregates can be subjected to various screening operations.

The vertically penetrating through holes 10 are formed at the support positions of the plate 7 of this embodiment. Thus, a culture solution can be sufficiently brought into contact with undergrown cells supported at the support positions of the plate 7. As a result, the plate 7 can preliminarily select undergrown cells before being sufficiently grown and form sufficiently grown cell aggregates by cultivating the undergrown cells at the support positions.

Second Embodiment

Since an object selecting device of a second embodiment is the same as in the first embodiment except that a holder is integrally provided to a plate 71 as shown in FIGS. 9A and 9B, only points of difference are described. FIGS. 9A and 9B are diagrams showing the holder of the second embodiment of the present disclosure.

As shown in FIG. 9A, legs 7a as the holder are integrally provided to a bottom surface 6 of the plate 71. The legs 7a extend downward from the bottom surface 6 and are provided to separate the bottom surface 6 of the plate 71 and an inner bottom part 2 of a container 4 in the container 4. The length of the legs 7a is not particularly limited and may be about equal to the length (height) of the spacer described in the first embodiment. The material of the legs 7a is not particularly limited and the legs 7a have only to be made of a material stable to liquid 3 in the container 4. In the case of integrally providing the legs 7a to the plate 71, the legs 7a may be made of the same material as the plate 7 (see first embodiment). The number and installed positions of the legs 7a are not particularly limited. For example, four legs 7a may be provided at four corners near an edge part of the bottom surface 6 of the plate 71.

As another example of the holder, hanging tools 7b as the holder are provided on a top surface 5 of a plate 72. The hanging tools 7b hang the plate 72 and hold the plate 72 in the liquid 3 of the container 4 in a state separated from the inner bottom part 2 of the container 4. The material of the hanging tools 7b is not particularly limited and is similar to that of the legs 7a. Further, the number and installed positions of the hanging tools 7b are not particularly limited. For example, the top surface 5 of the plate 72 may be fixed by the hanging tools 7b at positions near four corners and the other ends of the hanging tools 7b may be fixed to a peripheral device (not shown) to hang the plate 72.

Third Embodiment

Figure 10:
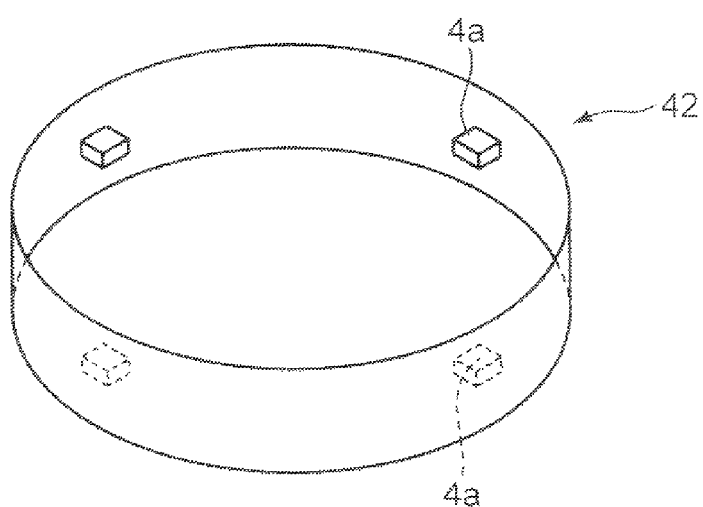
FIG. 10 is a diagram showing a holder of a third embodiment of the present disclosure.

Since an object selecting device of a third embodiment is the same as in the first and second embodiments except that a holder is formed of projections 4a provided on a container 4 as shown in FIG. 10, only points of difference are described. FIG. 10 is a diagram showing the holder of the third embodiment of the present disclosure.

As shown in FIG. 10, the container 42 is provided with projections 4a projecting inwardly of the container 42. The projections 4a horizontally project at positions below the liquid level of liquid 3 stored in the container 42. The projections 4a come into contact with a bottom surface 6 of a plate 7 and hold the bottom surface 6 of the plate 7 so that the bottom surface 6 is separated from an inner bottom part 2 of the container 42 when the plate 7 is immersed into the liquid 3. A distance from the inner bottom part 2 of the container 42 to the projections 4a is not particularly limited and may be about equal to the length (height) of the spacer described in the first embodiment. The material of the projections 42a is not particularly limited and the projections 42a have only to be made of a material stable to liquid 3 in the container 42. In the case of integrally providing the projections 4a to the container 42, the projections 4a may be made of the same material as the container 42. The number and installed positions of the projections 4a are not particularly limited. For example, as shown in FIG. 10, the inwardly projecting projections 4a can be provided at four positions having the same height in the case of using a flat glass dish as the container 42. In this case, the plate 7 is held by the contact of the projections 4a provided at four positions and the bottom surface 6 of the plate 7.

Note that the plate 7 may not be possibly held by the projections 4a at four positions as shown in FIG. 10 if the plate 7 is sufficiently smaller than the container 42. In such a case, the plate 7 may be held by providing projections 4a, which can support the plate 7 without closing the openings at bottom surface sides of through holes 10, at any positions of the container 42.

Besides, an edge part may be provided on the inner side surface of the container 42 and the plate 7 may be held by holding the bottom surface 6 of the plate 7 in contact with the edge part if the container 42 is a cylindrical glass dish.

Fourth Embodiment

Figure 12:
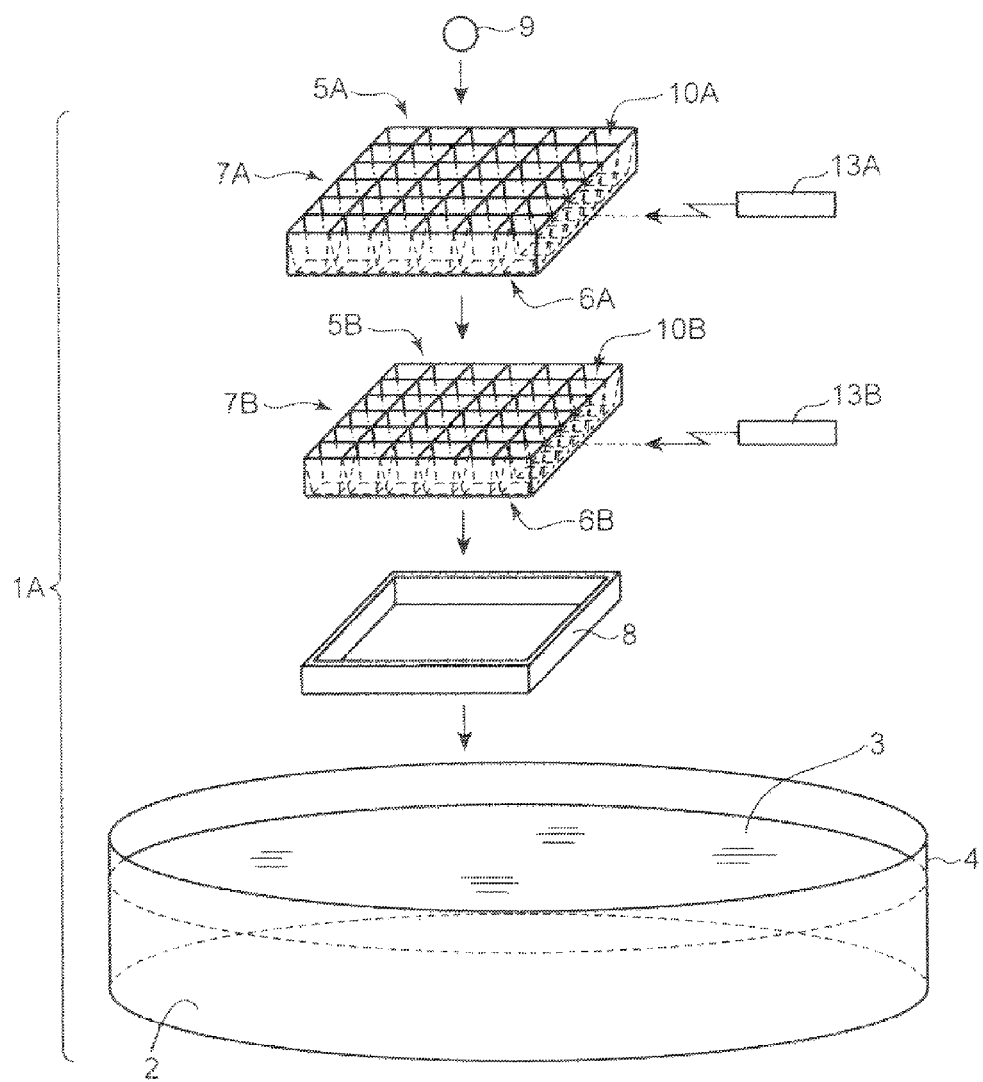
FIG. 12 is a diagram showing the configuration of an object selecting device of a fourth embodiment of the present disclosure.

Since an object selecting device 1A of a fourth embodiment is the same as the object selecting device 1 of the first embodiment except that two plates are used by being placed one over the other as shown in FIG. 12, only points of difference are described. FIG. 12 is a diagram showing the configuration of the object selecting device 1A of the fourth embodiment of the present disclosure.

The object selecting device 1A includes two plates 7A, 7B. As shown in FIG. 12, the plates 7A, 7B are used by being placed one over the other and immersed in a container 4 storing liquid 3.

A case is described as an example where an opening area at bottom sides of through holes 10A formed in the plate 7A is larger than that at bottom sides of through holes 10B formed in the plate 7B. Two types of selection objects 9 having different diameters can be simultaneously selected by placing the plate 7A on the plate 7B as shown in FIG. 12. Specifically, selection objects having relatively large diameters can be selected using the plate 7A and those having relatively small diameters can be selected from objects having passed through the through holes 10A of the plate 7A.

Note that although a mode in which two plates are used by being placed one over the other is illustrated in this embodiment, the number of the plates is not particularly limited and may be three or more.

Selection Method

Next, the object selecting method of this embodiment is described. The object selecting method of this embodiment is an object selecting method for selecting selection objects from a collection of objects including the selection objects, and includes an immersion step, a precipitation step and an arrangement step. Each step is described below.

Immersion Step

The immersion step is a step of immersing a plate having a top surface and a bottom surface and configured to support selection objects and a holder configured to hold the plate with the bottom surface of the plate and an inner bottom part of a container separated in a container storing liquid. The container, the plate and the holder are not described since they are the same as those described in detail in the description of the object selecting device 1.

Precipitation Step and Arrangement Step

The precipitation step is a step of adding the collection of objects including the selection objects to the liquid from a side of the top surface of the plate and causing the collection of objects to precipitate along the direction of gravity into through holes formed in the plate, arranged at support positions where the selection objects are supported and including tapered portions on the inner wall surfaces thereof, the opening area at the upper ends of the tapered portions being larger than that at the lower ends of the tapered portions.

Further, the arrangement step is a step of bringing the selection objects out of the collection of objects precipitating in the through holes into contact with the tapered portions and supporting them at the support positions.

The collection of objects and the through holes are not described since they are the same as those described above. A procedure of selecting and arranging the selection objects is described below. FIGS. 3A to 3D are diagrams showing a procedure of selecting the selection objects 9 in the object selecting device 1.

As shown in FIG. 3A, the plate 7 is immersed in the container 4 storing the liquid 3 via the spacer 8. FIG. 3A is a diagram of the plate 7 to be immersed into the container 4 storing the liquid 3 and the spacer 8 configured to hold the bottom surface 6 of the plate 7 in the state separated from the inner bottom part 2 of the container 4. In this way, the plate 7 is immersed in the liquid 3 in advance in a state where nothing is supported at the support positions. This enables the selection objects 9 to be selected in the liquid 3 and prevents the selection objects 9 included in the collection of objects M such as a cell culture solution from being exposed to outside air and being dried.

Subsequently, as shown in FIG. 3B, the collection of objects M is added to the liquid 3 from the side of the top surface 5 of the plate 7 immersed in the liquid 3. FIG. 3B is a diagram showing a state where the collection of objects M including the selection objects 9 is added to the liquid 3 from the side of the top surface 5 of the plate 7.

A method for adding the collection of objects M is not particularly limited, but the collection of objects M is preferably gently added from a position close to the liquid level or directly added to the liquid 3 using a pipette or the like when being added to the liquid 3 in order to eliminate the drying of the selection objects 9 and a physical impact. The collection of objects M added into the liquid 3 gently precipitates with gravity while being dispersed in the liquid 3. Thus, a physical impact on the selection objects 9 is reduced.

Subsequently, as shown in FIG. 3C, the collection of objects M precipitates in the liquid 3 with gravity and reaches the top surface 5 of the plate 7. FIG. 3C is a diagram showing a state where the collection of objects M added to the liquid 3 are precipitating in the through holes 10 along the direction of gravity and the collection of objects M have precipitated in a plurality of arranged through holes 10 of the plate 7. As described above, out of the collection of objects M having reached the top surface 5 of the plate 7 with gravity, the selection objects 9a and the non-objects 12a in contact with the tapered portions 11 are introduced into the through holes 10 while descending along the tapered portions 11.

Since the diameters of the non-objects 12a are smaller than the opening area at the lower ends of the tapered portions 11, the non-objects 12a pass through the through holes 10. The non-objects having passed through the through holes (non-objects 12b) precipitate to the inner bottom part 2 of the container.

On the other hand, as shown in FIG. 3D, the objects (selection objects 9c) having larger diameters than the opening area at the lower ends of the tapered portions 11 out of the collection of objects M precipitating into the through holes 10 are supported by the tapered portions 11 in contact with the inner wall surfaces of the tapered portions 11 and the through holes 10 and arranged on the plate 7.

Vibration Step

The object selecting method of this embodiment preferably further includes a vibration step.

Figure 11:
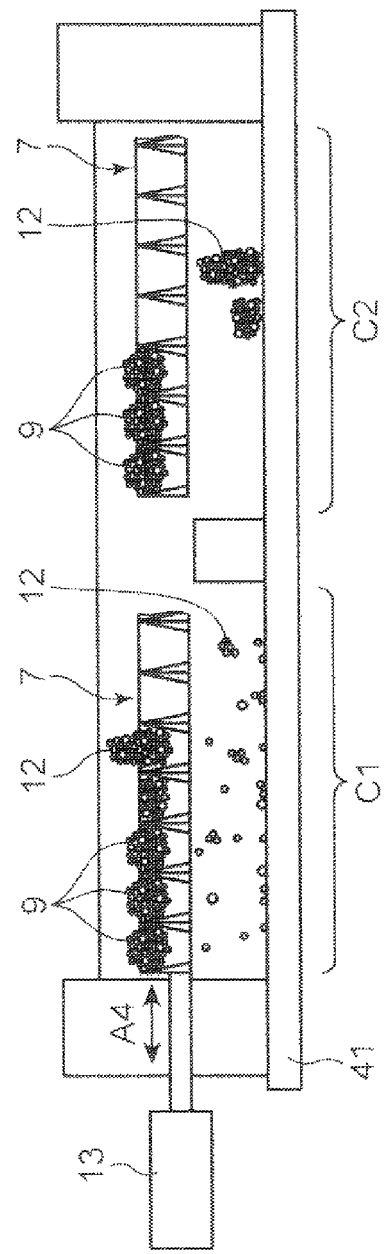
FIG. 11 is a diagram showing a vibration generation process in an object selecting method of the present disclosure.

The vibration step is a step of applying vibration to the plate to prompt the selection objects to be introduced to the support positions in the precipitation step or the arrangement step. The vibration generation mechanism 13 described above in the description of the object selecting device 1 can be used to apply vibration to the plate. The container 41 provided with the vibration generation mechanism 13 is described in more detail with reference to FIG. 11. FIG. 11 is a diagram showing a vibration generation step.

As shown in FIG. 11, the vibration generation mechanism 13 is connected to the plate 7 and vibrates the plate 7 in a planar direction. Reference numeral A4 denotes a vibrating direction of the plate 7 by the vibration generation mechanism 13. Note that the vibrating direction may be a direction other than the planar direction and may be, for example, a vertical direction, both the planar direction and the vertical direction or an irregular direction.

As shown in FIG. 11, in a cell capture chamber C1, the selection objects 9 described above are selected and vibration is applied to the plate 7 by the vibration generation mechanism 13 to select and remove objects having different diameters. A state of selection is obtained mainly by observing the presence or absence of the objects supported by the plate 7 by a determination mechanism (not shown) provided above or below the container 41. At this point in time, the non-objects 12 having diameters smaller than the opening area at the lower ends of the tapered portions are removed and the selection objects 9 are selected in the tapered portions 11. However, at this point in time, there is a possibility that objects having larger diameters or having distorted shapes are supported by the plate 7 besides the objects having a desired shape. Thus, the plate 7 is moved to an adjacent cell selection chamber C2 and further selection proceeds based on the shape.

In the cell selection chamber C2, the shapes of the objects supported by the plate 7 are observed by the determination mechanism (not shown) provided above or below the container 41. The determination mechanism is used after being appropriately moved from a position of observation in the cell capture chamber C1, but determination mechanisms corresponding to the respective chambers may also be prepared.

Although an observation method by the determination mechanism is not particularly limited, the substantially transparent objects can be clearly observed, for example, by using a phase-contrast microscope. Besides, if the selection objects 9 are dyed with a fluorescent dye such as trypan blue, they can be observed by a fluorescence microscope. As a result, if the selection objects 9 are, for example, cell aggregates, cell aggregates having larger diameters than the desired diameter, defective cell aggregates including dead cells and the like are newly determined as the non-objects 12. The determined non-objects 12 are manually removed by the user or, if the selection nozzle 14 described above is automated, the selection nozzle 14 is controlled not to extract the non-objects 12 as the selection objects 9.

Only the selection objects 9 are supported by the plate 7 having the non-objects 9 removed therefrom. The supported selection objects can be collected such as by vertically inverting the plate or can be extracted through an extraction step described below.

Extraction Step

The object selecting method of this embodiment preferably further includes the extraction step.

The extraction step is a step of extracting the supported selection objects from the plate. The selection nozzle described above in the description of the object selecting device 1 can be used to extract the selection objects from the plate. The selection nozzle is not described since it is the same as the one described above. The selection objects extracted using the selection nozzle may be, for example, directly subjected to various tests or may be arranged on a separately prepared plate and temporarily stored.

As described above, according to the object selecting method of this embodiment, it is possible to support only the selection objects having the predetermined shape out of the collection of objects having different shapes by the tapered portions and allow the non-objects other than the selection objects to precipitate to the inner bottom part of the container. Further, in the case of extracting the selection objects supported by the tapered portions such as by suction, the non-objects precipitated on the inner bottom part of the container are not erroneously extracted since the plate is held separated from the inner bottom part of the container by the holder.

Note that the aforementioned specific embodiments mainly include disclosures having the following configurations.

An object selecting device according to one aspect of the present disclosure includes a container including an inner bottom part and configured to store liquid, a plate having a top surface and a bottom surface and configured to support a selection object by being immersed into the liquid stored in the container, and a holder configured to hold the plate in a state where the bottom surface of the plate and the inner bottom part of the container are separated, wherein the plate includes a through hole at a support position for the selection object, the through hole includes a tapered portion configured to allow the selection object to precipitate along a direction of gravity and supporting the selection object in contact with the inner wall surface of the through hole in a state where the plate is immersed in the liquid in the container, and an opening area at the upper end of the tapered portion is larger than an opening area at the lower end of the tapered portion.

In the present disclosure, by adopting such a configuration, only the selection object having a predetermined shape out of the collection of objects having different shapes is supported by the tapered portion and non-objects other than the selection object are allowed to precipitate to the inner bottom part of the container. Further, since the plate is held separated from the inner bottom part of the container by the holder in the case of extracting the selection object supported by the tapered portion such as by suction, the non-objects precipitated on the inner bottom part of the container are not erroneously extracted.

The plate preferably includes a plurality of the through holes arranged in a matrix.

In the present disclosure, by adopting such a configuration, a plurality of selection objects having the predetermined shape can be simultaneously selected, time and labor can be drastically saved as compared with the case where the selection objects are individually selected and operation efficiency can be improved. Further, in the case of extracting the selection objects, for example, by a nozzle or the like, the preparation of a plurality of nozzles corresponding to the arrangement of the through holes can contribute to the automation of the device. As a result, the device can be used for high-throughput screening and the like and a work amount can be drastically reduced.

The through hole preferably has a frustum shape.

In the present disclosure, by adopting such a configuration, the selection object is easily introduced into the through hole since the inner side surface of the through hole serves as the inclined tapered portion. Further, the selection object having a substantially spherical shape is easily selected, for example, as compared with the case where the tapered portion is provided on a part of the inner wall surface of the through hole.

The through hole is preferably shaped to form a clearance capable of allowing the liquid to flow from the bottom surface side to the top surface side in a state where the selection object is supported by the plate.

In the present disclosure, by adopting such a configuration, the selection object can be easily picked up by an extractor since it is prevented from being closely fitted into the through hole.

A ratio of the opening area at the lower end of the tapered portion to the opening area at the upper end of the tapered portion is preferably 0.11 to 0.94.

In the present disclosure, by adopting such a configuration, even if there is a slight flow of the liquid in the container, the selection object supported by the plate can be more reliably supported by the plate without inadvertently flowing out of the through hole. Further, it is possible to capture the plate, the selection object and a nozzle as the extractor within a depth of field of a lens provided in a phase-contrast microscope, for example, in the case of observing the supported selection object from below the container by the phase-contrast microscope. Thus, a user can not only easily confirm whether or not the selection object is supported by the plate and the shape of the supported selection object, but also easily confirm the position of the selection object and that of the nozzle at the time of extraction by the extractor.

The container and the plate are preferably made of a translucent material.

In the present disclosure, by adopting such a configuration, the selection object can be continuously confirmed, for example, by the phase-contrast microscope from above or below the container and operation efficiency can be improved.

The selection object is preferably a bio-based cell.

By adopting such a configuration, the present disclosure can be applied to the bio-based cell, which is an object with a large shape deviation, and can provide a device capable of contributing to an improvement in operation efficiency in the fields of bio-related technology and medicine.

The selection object is preferably a bio-related cell aggregate.

The bio-based cell aggregate can provide a result considering functions of individual cells as compared with a test result obtained using one cell since a biosimilar environment considering interactions among cells is reconfigured in the cell aggregate, and experiment conditions can be made uniform in accordance with an environment in a biological body. Thus, by adopting such a configuration, the present disclosure can provide a device capable of obtaining a highly reliable result in the fields of bio-related technology and medicine.

It is preferable to further include a vibration generator configured to apply vibration to the plate.

In the present disclosure, by adopting such a configuration, even if there are selection objects held on the plate without being supported by the plate, those selection objects can be prompted to move to the support positions by applying vibration to them. Further, if elliptical non-objects not having a substantially spherical shape and the like are caught in the through holes, they can be prompted to pass through the through holes and precipitate by applying vibration. Furthermore, since the vibration generator is provided not for the container, but for the plate, cell aggregates already precipitated on the inner bottom part of the container and having distorted shapes and non-objects composed of one cell are not blown up. Thus, the non-objects are not extracted in extracting the selection objects by the extractor.

It is preferable to further include an extractor configured to extract the selection object from the plate.

In the present disclosure, by adopting such a configuration, the remaining plate can be reused since the selection object can be extracted from the plate and moved to a subsequent step. Particularly, by automating the extractor, operation efficiency can be improved. Note that the reuse of the plate 7 is not essential and the plate 7 can be disposable.

An object selecting method according to another aspect of the present disclosure is an object selecting method for selecting a selection object from a collection of objects including the selection object and includes an immersion step of immersing a plate having a top surface and a bottom surface and configured to support a selection object and a holder configured to hold the plate with the bottom surface of the plate and an inner bottom part of a container separated in the container including the inner bottom part and storing liquid, a precipitation step of adding a collection of objects including the selection object to the liquid from a side of the top surface of the plate and causing the collection of objects to precipitate along a direction of gravity into a through hole formed in the plate, arranged at a support position where the selection object is supported and including a tapered portion on the inner wall surface thereof, an opening area at the upper end of the tapered portion being larger than an opening area at the lower end of the tapered portion, and an arrangement step of bringing the selection object out of the collection of objects precipitating in the through hole into contact with the tapered portion and supporting the selection object at the support position.

In the present disclosure, by adopting such a configuration, only the selection object having a predetermined shape out of the collection of objects having different shapes is supported by the tapered portion and non-objects other than the selection object are allowed to precipitate to the inner bottom part of the container. Further, since the plate is held separated from the inner bottom part of the container by the holder in the case of extracting the selection object supported by the tapered portion such as by suction, the non-objects precipitated on the inner bottom part of the container are not erroneously extracted.

It is preferable to further include a vibration step of applying vibration to the plate to prompt the selection object to be introduced to the support position in the precipitation step or the arrangement step.

In the present disclosure, by adopting such a configuration, even if there are selection objects held on the plate without being supported by the plate, those selection objects can be prompted to move to support positions by applying vibration to them. Further, since the vibration generator is provided not for the container, but for the plate, cell aggregates already precipitated on the inner bottom part of the container and having distorted shapes and non-objects composed of one cell are not blown up by the vibration, and the non-objects are not extracted in extracting the selection objects.

It is preferable to further include an extraction step of extracting the supported selection object from the plate.

In the present disclosure, by adopting such a configuration, the remaining plate can be reused since the selection object can be extracted from the plate and moved to a subsequent step. Particularly, by automating the extractor, operation efficiency can be improved.

The invention claimed is:

1. An object selecting device, comprising:
   a container including an inner bottom part and configured to store liquid;
   a plate having a top surface and a bottom surface and configured to support a selection object by being immersed into the liquid stored in the container; and
   a holder configured to hold the plate in a state where the bottom surface of the plate and the inner bottom part of the container are separated,
   the plate including a through hole at a support position for the selection object; and
   the through hole being configured to allow the selection object to precipitate along a direction of gravity and including a tapered portion for supporting the selection object in contact with an inner wall surface of the through hole in a state where the plate is immersed in the liquid in the container, an opening area at an upper end of the tapered portion being larger than an opening area at a lower end of the tapered portion.

2. The object selecting device according to claim 1, wherein:
   the plate includes a plurality of the through holes at support positions for the selection objects; and
   the plurality of through holes are so arranged adjacent to each other that the upper end of the tapered portion is in contact with the upper end of the tapered portion of an adjacent through hole.

3. The object selecting device according to claim 1, wherein the plate includes a plurality of through holes arranged in a matrix.

4. The object selecting device according to claim 1, wherein the through hole has a frustum shape.

5. The object selecting device according to claim 1, wherein the through hole is shaped to form a clearance capable of allowing the liquid to flow from the bottom surface to the top surface in a state where the selection object is supported by the plate.

6. The object selecting device according to claim 1, wherein a ratio of the opening area at the lower end of the tapered portion to the opening area at the upper end of the tapered portion is 0.11 to 0.94.

7. The object selecting device according to claim 1, wherein the container and the plate are made of a translucent material.

8. The object selecting device according to claim 2, wherein the holder is a hollow spacer which is placed on the inner bottom part of the container and holds the plate thereon.

9. The object selecting device according to claim 2, wherein:
   the holder is a leg unit provided on the bottom surface of the plate; and the plate is held separated from the inner bottom part of the container by the leg unit.

10. The object selecting device according to claim 2, wherein:
   the holder is a hanging tool provided on the top surface of the plate; and
   the plate is held separated from the inner bottom part of the container by the hanging tool.

11. The object selecting device according to claim 1, wherein the selection object is a bio-based cell.

12. The object selecting device according to claim 11, wherein the selection object is a bio-related cell aggregate.

13. The object selecting device according to claim 1, further comprising a vibration generator configured to apply vibration to the plate.

14. The object selecting device according to claim 1, further comprising an extractor configured to extract the selection object from the plate.

15. An object selecting method for selecting a selection object from a collection of objects containing the selection object, comprising:
   storing liquid in a container, the container having an inner bottom part;
   immersing a plate in the liquid in the container, the plate having a top surface and a bottom surface and the plate being configured to support a selection object;
   placing a holder in the container, the holder being configured to hold the plate with the bottom surface of the plate separated in the container from the inner bottom part;
   adding a collection of objects including the selection object to the liquid from a side of the top surface of the plate and causing the collection of objects to precipitate along a direction of gravity into a through hole formed in the plate, the through hole including a tapered portion on an inner wall surface thereof, an opening area at an upper end of the tapered portion being larger than an opening area at a lower end of the tapered portion; and
   bringing the selection object out of the collection of objects precipitating in the through hole into contact with the tapered portion and supporting the selection object at a support position.

16. The object selecting method according to claim 15, further comprising applying vibration to the plate to prompt the selection object to be introduced to the support position.

17. The object selecting method according to claim 15, further comprising extracting the supported selection object from the plate.

* * * * *